United States Patent [19]
Kimura et al.

[11] Patent Number: 6,114,319
[45] Date of Patent: Sep. 5, 2000

[54] COMPOSITIONS CONTAINING DIFLUPREDNATE

[75] Inventors: Masako Kimura, Kakogawa; Shin-ichi Yasueda, Kobe; Masazumi Yamaguchi, Kobe; Katsuhiro Inada, Kobe, all of Japan

[73] Assignees: Senju Pharmaceutical Co., Ltd.; Mitsubishi Chemical Corporation, both of Japan

[21] Appl. No.: 09/076,124

[22] Filed: May 12, 1998

[30] Foreign Application Priority Data

May 14, 1997 [JP] Japan ..................................... 9-124415

[51] Int. Cl.⁷ ..................................................... A61K 31/56
[52] U.S. Cl. ............................................. 514/177; 514/912
[58] Field of Search ...................................... 514/177, 912

[56] References Cited

U.S. PATENT DOCUMENTS 3,780,177   12/1973   Ercoli et al. .
4,427,670   1/1984    Ofuchi et al. .
5,556,848   9/1996    Kimura et al. .......................... 514/179

FOREIGN PATENT DOCUMENTS 5-43465      2/1993   Japan .
WO98/30221   7/1998   WIPO .

*Primary Examiner*—Zohreh Fay
*Attorney, Agent, or Firm*—Wenderoth, Lind & Ponack, L.L.P.

[57] ABSTRACT

The present invention relates to a liquid composition comprising difluprednate, oil, water and an emulsifier. The composition of the present invention has superior antiinflammatory action and antiallergic action. The composition of the present invention shows superior transfer to a lesion and uniform drug distribution upon administration, as compared to conventional preparations containing difluprednate, so that it shows sufficient efficacy in a smaller dose. The inventive composition is associated with extremely less uncomfortable feeling and foreign sensation upon administration, as compared to conventional preparations containing difluprednate, and it can be administered easily to local sites of eye, nose, ear and the like.

17 Claims, No Drawings

COMPOSITIONS CONTAINING DIFLUPREDNATE

TECHNICAL FIELD OF THE INVENTION

The present invention relates to a liquid composition containing difluprednate, oil, water and an emulsifier. More particularly, the present invention relates to a liquid composition containing difluprednate, which permits uniform drug distribution and superior transfer of difluprednate into a lesion, and which is associated with less uncomfortable feeling and foreign sensation.

BACKGROUND OF THE INVENTION

Difluprednate (6α,9α-difluoroprednisolone 17-butyrate 21-acetate) is an antiinflammatory steroid which is known to show superior antiinflammatory action by percutaneous administration (U.S. Pat. Nos. 3,780,177, 3,784,692). In addition, difluprednate is reported to show superior antiinflammatory action and antiallergic action by percutaneous administration and subcutaneous administration (Pharmacometrics, 29 (3), 343–353 (1985), Pharmacometrics, 29 (3), 355–362 (1985)). Therefore, difluprednate is mainly used as a therapeutic drug in the preparation form of ointment, cream and the like for skin disorders.

On the other hand, when difluprednate is administered locally to an eye, nose, ear or the like, a liquid dosage form, such as an eye drop, a nasal drop, an ear drop and the like, is desirable. However, inasmuch as difluprednate has extremely low solubility in water, it is difficult to prepare a stable eye drop, nasal drop, ear drop or the like, containing difluprednate in a concentration effective for treatment, and a dosage form of an aqueous suspension has been proposed for the administration to the local sites as mentioned above (U.S. Pat. No. 5,556,848).

When, for example, an aqueous suspension of difluprednate is used as an eye drop, however, common problems associated with aqueous ophthalmic suspensions, namely, difficulty in sustaining uniform drug distribution upon instillation, uncomfortable feeling caused by solid entering into the eye and inability to completely eliminate foreign sensation, have been pointed out. In addition, since difluprednate is an antiinflammatory steroid, it is on the one hand sufficiently effective for the treatment of inflammatory diseases, allergic diseases and the like, but on the other hand associated with side effects. Thus, there is a need for the development of a dosage form permitting quick and uniform transfer of an effective amount of difluprednate and causing less side effects, in view of a case where a part (e.g., inner ocular area) distant from the instillation site (e.g., outer ocular area) has an inflammation.

SUMMARY OF THE INVENTION

As mentioned above, since difluprednate has superior antiinflammatory action and antiallergic action, it is useful for the prophylaxis and treatment of various inflammatory diseases and allergic diseases. When it is applied for the treatment of diseases in the eye, nose, ear and the like, it needs to be formulated into an administration dosage form permitting instillation in the eye, nose, ear and the like. When difluprednate is used in the form of an aqueous suspension for the treatment of these local diseases, however, the above-mentioned problems in terms of transfer of the drug to the lesion, distribution of the drug and feeling in use, such as uncomfortable feeling and foreign sensation, remain to be solved.

It is therefore an object of the present invention to provide a composition containing difluprednate, which shows superior transfer of the drug to the lesion, uniform drug distribution upon administration, less uncomfortable feeling and foreign sensation upon administration, and less side effects.

According to the present invention, it has now been found that a dosage form of a liquid composition containing difluprednate, oil, water and an emulsifier results in quick transfer of a large amount of difluprednate, uniform drug distribution and extremely reduced levels of uncomfortable feeling and foreign sensation upon local administration to the eye, nose, ear and the like. Inasmuch as difluprednate can be transferred smoothly, administration of a small dose thereof is sufficient to bring about efficacy, whereby side effects can be suppressed.

That is, the present invention provides the following.

(1) A difluprednate liquid composition comprising difluprednate, oil, water and an emulsifier.
(2) The composition of (1) above, comprising 10–100,000 parts by weight of oil, 100–100,000 parts by weight of water and 10–100,000 parts by weight of the emulsifier, per part by weight of difluprednate.
(3) The composition of (1) above, comprising 10–10,000 parts by weight of oil, 100–50,000 parts by weight of water and 10–10,000 parts by weight of the emulsifier, per part by weight of difluprednate.
(4) The composition of (1) above, comprising 10–5,000 parts by weight of oil, 500–50,000 parts by weight of water and 10–5,000 parts by weight of the emulsifier, per part by weight of difluprednate.
(5) The composition of (1) above, wherein the oil comprises a fatty acid ester of glycerol.
(6) The composition of (5) above, wherein the fatty acid ester of glycerol is a member selected from the group consisting of castor oil, peanut oil, cotton seed oil, soybean oil, olive oil and a medium chain fatty acid triglyceride.
(7) The composition of (1) above, wherein the emulsifier comprises a surfactant.
(8) The composition of (7) above, wherein the surfactant is a nonionic surfactant.
(9) The composition of (8) above, wherein the nonionic surfactant is a member selected from the group consisting of polyoxyethylene hydrogenated castor oil and a polyoxyethylenesorbitan fatty acid ester.
(10) The composition of (9) above, wherein the polyoxyethylenesorbitan fatty acid ester is a member selected from the group consisting of polyoxyethylene-sorbitan monooleate, polyoxyethylenesorbitan monolaurate, polyoxyethylene-sorbitan monopalmitate and polyoxyethylenesorbitan monostearate.
(11) The composition of any one of (1) to (4) above, which is an oil-in-water type emulsion.
(12) The composition of any one of (1) to (4) above, which is in the form of an eye drop, a nasal drop or an ear drop.

DETAILED DESCRIPTION OF THE INVENTION

The composition of the present invention contains difluprednate, oil, water and an emulsifier. The oil usable in the present invention may be any as long as it is applicable to the eye, and is low toxic and less irritant to the eye. Preferably, an oil containing a fatty acid ester of glycerol, such as castor oil, peanut oil, cotton seed oil, soybean oil, olive oil, medium chain fatty acid triglycerides (e.g., Miglyol, trademark, manufactured by Mitsuba Boeki) and the like, is used. More preferably, castor oil, medium chain fatty acid triglycerides (e.g., Miglyol) and the like, in which difluprednate is highly soluble, can be used.

In the present invention, a surfactant, such as a nonionic surfactant having surface activating capability and the like, may be contained as an emulsifier. Examples of the nonionic surfactant include polyoxyethylene hydrogenated castor oils and polyoxyethylenesorbitan fatty acid esters, preferably polyoxyethylenesorbitan monooleates, polyoxyethylenesorbitan monolaurates, polyoxyethylenesorbitan monopalmitates, polyoxyethylenesorbitan monostearates and the like.

While the ratio of each of the above-mentioned ingredients in the composition of the present invention is not particularly limited, it is preferable that oil be contained in a proportion of 10–100,000 parts by weight, water in a proportion of 100–100,000 parts by weight and emulsifier in a proportion of 10–100,000 parts by weight, all per part by weight of difluprednate; preferably in the proportions of oil 10–10,000 parts by weight, water 100–50,000 parts by weight and emulsifier 10–10,000 parts by weight, all per part by weight of difluprednate; and particularly preferably in the proportions of oil 10–5,000 parts by weight, water 500–50,000 parts by weight and emulsifier 10–5,000 parts by weight, all per part by weight of difluprednate.

It is particularly preferable that the weight ratio of water (which is a medium) to oil be 4:1–99:1.

The composition of the present invention may contain a water soluble polymer for enhanced stabilization of emulsion. Examples of the water soluble polymer include povidone (polyvinylpyrrolidone), polyvinyl alcohol, hydroxyethylcellulose, hydroxypropylcellulose, methylcellulose, hydroxypropylmethylcellulose, carboxymethylcellulose and salt thereof, and the like.

The composition of the present invention may contain a buffer. Examples of the buffer include acetates such as sodium acetate and the like, phosphates such as sodium dihydrogenphosphate, disodium hydrogenphosphate, potassium dihydrogenphosphate, dipotassium hydrogenphosphate and the like, ε-aminocaproic acid, amino acid salts such as sodium glutamate and the like, boric acid and salt thereof, citric acid and salt thereof, and the like.

The composition of the present invention may contain a preservative. Examples of the preservative include quaternary ammonium salts such as benzalkonium chloride, benzethonium chloride and the like; cationic compounds such as chlorhexidine gluconate and the like; p-hydroxybenzoates such as methyl p-hydroxybenzoate, propyl p-hydroxybenzoate and the like; alcohol compounds such as chlorobutanol, benzyl alcohol and the like; sodium dehydroacetate; thimerosal; sorbic acid; and the like.

The composition of the present invention may contain an isotonizing agent. Examples of the isotonizing agent include sodium chloride, glycerol, glucose, mannitol, sorbitol and the like.

The composition of the present invention may also contain various additives, such as a stabilizer, an antioxidant, a chelating agent, a pH adjusting agent, a thickener and the like. Examples of the antioxidant include ascorbic acid and salt thereof, tocopherol, sodium thiosulfate, sodium hydrogensulfite, pyruvic acid and salt thereof, and the like. The chelating agent is exemplified by sodium edetate, citric acid and salt thereof, and the like. Examples of the pH adjusting agent include hydrochloric acid, phosphoric acid, acetic acid, sulfuric acid, sodium hydroxide, potassium hydroxide, sodium carbonate, sodium hydrogencarbonate, aqueous ammonia and the like.

The composition of the present invention can be provided as an aqueous preparation of oil-in-water type (O/W type) emulsion, microemulsion and the like.

An oil drop of the composition of the present invention has a median size of preferably 5–0.0001 $\mu$m, more preferably 1–0.001 $\mu$m, and particularly preferably 1–0.01 $\mu$m. The median size can be measured by an apparatus for particle size distribution.

The composition of the present invention preferably has a pH of 3–8. More preferable pH is 4–7, at which difluprednate is more stabilized.

The composition of the present invention is prepared by emulsifying oil, in which difluprednate has been dissolved, and water, using an emulsifier according to a known method. For example, an emulsifier and the above-mentioned additive, as necessary, are added to water, its pH is adjusted to 3–8 with a pH adjusting agent, and oil, in which difluprednate has been dissolved, is added to give an emulsion. For uniform emulsification, a known means, such as a homomixer, homogenizer, microfluidizer, high pressure homogenizer and the like, may be used.

The composition of the present invention is preferably used as a preparation for local administration to the eye, nose or ear, and more preferably used as an eye drop, nasal drop or ear drop.

The composition of the present invention has superior antiinflammatory action and antiallergic action. In addition, it shows superior transfer of difluprednate in a large amount, uniform drug distribution and extremely reduced levels of uncomfortable feeling and foreign sensation upon administration. In addition, administration of a small dose thereof is sufficient to produce efficacy, whereby side effects can be suppressed. Therefore, it is useful for the prophylaxis and treatment of various inflammatory diseases and allergic diseases, such as allergic conjunctivitis, vernal conjunctivitis, blepharitis marginalis, catarrhal conjunctivitis, uveitis and the like, and it can be beneficially used for local administration to the eye, nose, ear and the like.

The composition of the present invention can be administered safely to mammals (e.g., human, dog, rabbit, cow, horse, monkey, cat, sheep, etc.).

While the dose of the composition of the present invention varies depending on the kind of disease, symptom, age and body weight of patients and the like, when it is administered to an adult, for example, the dose is preferably one or two drops per instillation in one eye according to the state of the disease, as an eye drop containing difluprednate in a concentration of about 0.005–0.1%, wherein the dose frequency is two to four times a day.

The present invention is described in more detail by way of Examples and Experimental Examples, which should not be construed as limiting the invention.

In the following Examples and Experimental Examples, the median size was measured by Shimadzu SALD-2000 laser diffraction apparatus for particle size distribution (dispersion medium: water, refractive index: 1.70–0.20i) upon addition of about 2 ml of the composition to be measured.

EXAMPLE 1

Difluprednate 0.05 g
Castor oil 5.0 g
Polysorbate 80 4.0 g
Concentrated glycerol 2.0 g Sodium acetate 0.01 g Boric acid 0.1 g Sodium edetate 0.02 g Sorbic acid 0.1 g Sodium hydroxide suitable amount Sterile purified water amount to make the total 100 ml (pH 6.0)

Sterile purified water was heated to about 70° C. and polysorbate 80, concentrated glycerol, sodium acetate, boric acid, sodium edetate and sorbic acid of the above formulation were added and dissolved. Its pH was adjusted to 6.0 with sodium hydroxide to give an aqueous phase. Separately, castor oil was heated to about 70° C. and difluprednate was added and dissolved to give an oil phase. The oil phase was added while stiring the aqueous phase with a homomixer to give a crude emulsion. This crude emulsion was finely divided in a microfluidizer and sterilized by filtration to give a composition of the present invention. The median size of the oil drop in the composition of the present invention was 0.06 µm.

EXAMPLE 2

Difluprednate 0.005 g

Castor oil 1.0 g

Polysorbate 80 0.5 g

Concentrated glycerol 2.2 g

Hydroxypropylmethylcellulose 0.1 g

Sodium acetate 0.05 g

Chlorobutanol 0.3 g

Hydrochloric acid suitable amount

Sterile purified water amount to make the total 100 ml (pH 4.0)

Sterile purified water was heated to about 70° C. and polysorbate 80, concentrated glycerol, hydroxypropylmethylcellulose, sodium acetate and chlorobutanol of the above formulation were added and dissolved. Its pH was adjusted to 4.0 with hydrochloric acid to give an aqueous phase. Separately, castor oil was heated to about 70° C. and difluprednate was added and dissolved to give an oil phase. The oil phase was added while stiring the aqueous phase with a homomixer to give a crude emulsion. This crude emulsion was finely divided in a microfluidizer and sterilized by filtration to give a composition of the present invention. The median size of the oil drop in the composition of the present invention was 0.12 µm.

EXAMPLE 3

Difluprednate 0.01 g

Miglyol 10.0 g

Polysorbate 80 5.0 g

Concentrated glycerol 2.2 g

ε-aminocaproic acid 0.05 g

Chlorhexidine gluconate 0.005 g

Sodium hydroxide suitable amount

Sterile purified water amount to make the total 100 ml (pH 5.5)

Sterile purified water was heated to about 70° C. and polysorbate 80, concentrated glycerol, ε-aminocaproic acid and chlorhexidine gluconate of the above formulation were added and dissolved. Its pH was adjusted to 5.5 with sodium hydroxide to give an aqueous phase. Separately, Miglyol was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.21 µm.

EXAMPLE 4

Difluprednate 0.1 g

Castor oil 20.0 g

Polyoxyethylene hydrogenated castor oil 60 5.0 g

Concentrated glycerol 2.2 g

Sodium glutamate 0.01 g

Methyl p-hydroxybenzoate 0.02 g

Propyl p-hydroxybenzoate 0.01 g

Sodium hydroxide suitable amount

Sterile purified water amount to make the total 100 ml (pH 5.0)

Sterile purified water was heated to about 70° C. and polyoxyethylene hydrogenated castor oil 60, concentrated glycerol, sodium glutamate, methyl p-hydroxybenzoate and propyl p-hydroxybenzoate of the above formulation were added and dissolved. Its pH was adjusted to 5.0 with sodium hydroxide to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 µm.

EXAMPLE 5

Difluprednate 0.05 g

Castor oil 8.0 g

Polysorbate 80 5.0 g

Polyvinyl alcohol 0.02 g

Concentrated glycerol 2.2 g

Sodium acetate 0.1 g

Benzalkonium chloride 0.01 g

Hydrochloric acid suitable amount

Sterile purified water amount to make the total 100 ml (pH 5.0)

Sterile purified water was heated to about 70° C. and polysorbate 80, polyvinyl alcohol, concentrated glycerol, sodium acetate and benzalkonium chloride of the above formulation were added and dissolved. Its pH was adjusted to 5.0 with hydrochloric acid to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 µm.

EXAMPLE 6

Difluprednate 0.01 g

Miglyol 5.0 g

Polysorbate 80 4.0 g

Concentrated glycerol 2.0 g

Sodium hydrogenphosphate 0.05 g

Sodium edetate 0.01 g

Benzalkonium chloride 0.005 g

Sodium hydroxide suitable amount

Sterile purified water amount to make the total 100 ml (pH 7.0)

Sterile purified water was heated to about 70° C. and polysorbate 80, concentrated glycerol, sodium hydrogenphosphate, sodium edetate and benzalkonium chloride of the above formulation were added and dissolved. Its pH was adjusted to 7.0 with sodium hydroxide to give an aqueous phase. Separately, Miglyol was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 μm.

EXAMPLE 7

Difluprednate 0.05 g

Castor oil 5.0 g

Polysorbate 80 4.0 g

Concentrated glycerol 2.2 g

Sodium acetate 0.05 g

Sodium edetate 0.02 g

Boric acid 0.1 g

Sorbic acid 0.1 g

Sodium hydroxide suitable amount

Sterile purified water amount to make the total 100 ml (pH 5.5)

Sterile purified water was heated to about 70° C. and polysorbate 80, concentrated glycerol, sodium acetate, sodium edetate, boric acid and sorbic acid of the above formulation were added and dissolved. Its pH was adjusted to 5.5 with sodium hydroxide to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 μm.

EXAMPLE 8

Difluprednate 0.01 g

Castor oil 5.0 g

Polysorbate 80 4.0 g

Concentrated glycerol 2.2 g

Sodium acetate 0.05 g

Sodium edetate 0.02 g

Boric acid 0.1 g

Sorbic acid 0.1 g

Sodium hydroxide suitable amount

Sterile purified water amount to make the total 100 ml (pH 5.5)

Sterile purified water was heated to about 70° C. and polysorbate 80, concentrated glycerol, sodium acetate, sodium edetate, boric acid and sorbic acid of the above formulation were added and dissolved. Its pH was adjusted to 5.5 with sodium hydroxide to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 μm.

EXAMPLE 9

Difluprednate 0.002 g

Castor oil 5.0 g

Polysorbate 80 4.0 g

Concentrated glycerol 2.2 g

Sodium acetate 0.05 g

Sodium edetate 0.02 g

Boric acid 0.1 g

Sorbic acid 0.1 g

Sodium hydroxide suitable amount

Sterile purified water amount to make the total 100 ml (pH 5.5)

Sterile purified water was heated to about 70° C. and polysorbate 80, concentrated glycerol, sodium acetate, sodium edetate, boric acid and sorbic acid of the above formulation were added and dissolved. Its pH was adjusted to 5.5 with sodium hydroxide to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 μm.

Experimental Example 1

The transfer into anterior chamber (intraocular transfer) of rabbits was compared between a difluprednate ophthalmic suspension and the composition of the present invention after a single instillation thereof.

A difluprednate ophthalmic suspension, which is a steroidal agent, has been already known to have significant inhibitory effect on rabbits with experimental uveitis. In this Experiment, transfer of difluprednate into anterior chamber (intraocular transfer) was compared between a difluprednate ophthalmic suspension and the composition of the present invention, in an attempt to improve intraocular transfer of difluprednate.

(1) Test Composition

The composition of the present invention and an ophthalmic suspension having the formulations shown in Table 1 were prepared as in the following.

[Composition of the Present Invention]

Sterile purified water (800 ml) was heated to about 70° C., and polysorbate 80 (40 g) and concentrated glycerol (26 g) were added and dissolved to give an aqueous phase. Separately, castor oil (50 g) was heated to about 70° C., and difluprednate (0.5 g) was added and dissolved to give an oil phase. The oil phase was added while stiring the aqueous phase with a homomixer to give a crude emulsion, and sterile purified water was added to make the total amount 1000 ml. This crude emulsion was finely divided in a microfluidizer. Sterilization by filtration gave the composition of the present invention.

[Ophthalmic Suspension]

Sterile purified water (800 ml) was heated to about 70° C. and hydroxypropylmethylcellulose (2 g) was added. After thorough dispersion, the mixture was cooled to about 30° C., and hydroxypropylmethylcellulose was added. Then, sodium acetate (1 g), sodium chloride (8 g) and benzalkonium chloride solution (10 w/v % 0.5 ml) were added and dissolved. Its pH was adjusted to 5.0 with hydrochloric acid and the mixture was sterilized by filtration. Difluprednate (1 g) was added and thoroughly suspended. Sterile purified water was added to make the total amount 1000 ml, whereby the ophthalmic suspension was obtained.

TABLE 1

(in 100 ml)

| Formulation | suspension (R.P.1) | composition of the present invention (R.P.2) |
| --- | --- | --- |
| Difluprednate | 0.1 g | 0.05 g |
| Sodium acetate | 0.1 g | — |
| HPMC (60SH50) | 0.2 g | — |
| Sodium chloride | 0.8 g | — |
| Benzalkonium chloride | 0.005 g | — |
| Hydrochloric acid | suitable amount | — |
| Sterile purified water | suitable amount | suitable amount |
| Castor oil | — | 5.0 g |
| Polysorbate 80 | — | 4.0 g |
| Concentrated glycerol | — | 2.6 g |
| pH | 5.0 | 6.5 |
| Median size | 4.0 μm | 0.16 μm |

(HPMC: hydroxypropylmethylcellulose)

(2) Test Animal

Male Japanese albino rabbits weighing about 2 kg and having no abnormalities in the eye were used. These rabbits were reared in a rearing chamber set to the conditions of room temperature 23±3° C. and relative humidity 55±10%, each chamber housing one rabbit. The rabbits were fed with solid feed (100 g per day, Labo RG-RO, NIHON NOSAN KOGYO K.K.) and allowed to have a free access to tap water.

(3) Test Method

The test composition (50 μl) was instilled in the eye, and one hour later, the rabbits were slaughtered with pentobarbital. Immediately after slaughter, anterior ocular segment was washed with physiological saline and aqueous humor was taken. Since difluprednate is deesterified at 21 position in aqueous humor and the like and metabolized into DFB (6α,9α-difluoroprednisolone 17-butyrate), DFB was measured by high performance liquid chromatography (HPLC) and taken as an index of difluprednate concentration in anterior chamber. The HPLC conditions were as follows.

HPLC conditions:

column: TSK gel ODS-80Ts mobile phase: 10 mM $NaH_2PO_4.2H_2O$(pH7)/$CH_3CN$=55/45 column temperature: 40° C.

flow rate: 1.3 ml/min wavelength: 240 nm amount injected: 50 μl

The DFB concentration in the anterior chamber of the eye of rabbits after one hour from a single instillation of the test composition is shown in Table 2.

TABLE 2

DFB concentration in aqueous humor

| | test composition | |
| --- | --- | --- |
| | suspension (R.P.1) | composition of the present invention (R.P.2) |
| DFB concentration (ng/ml) | 19.15 ± 2.8 | 42.95 ± 6.5 |

Each value shows mean ± S.E. (N = 7–8).

When difluprednate was prepared into a composition of the present invention, the amount of intraocular transfer was 42.95 ng/ml, despite the fact that the drug concentration in the composition was half the amount thereof in the suspension. This value was about 2.2 times greater than that in the case of the suspension, and significant difference was found. The above results reveal that the composition of the present invention shows efficacy greater than that afforded by a suspension even in a smaller dose.

Thus, the composition of the present invention has superior antiinflammatory action and antiallergic action.

In addition, the composition of the present invention shows superior transfer to a lesion as well as uniform drug distribution upon administration, as compared to conventional preparations containing difluprednate, so that it shows sufficient efficacy in a smaller dose. The inventive composition is associated with extremely less uncomfortable feeling and foreign sensation upon administration, as compared to conventional preparations containing difluprednate, and it can be administered easily to local sites of eye, nose, ear and the like.

This application is based on application No. 21807/1997 filed in Japan, the content of which is incorporated hereinto by reference.

What is claimed is:

1. A difluprednate emulsion comprising difluprednate, oil comprising a fatty acid ester of glycerol, water and an emulsifier.

2. The emulsion of claim 1, comprising 10–100,000 parts by weight of oil, 100–100,000 parts by weight of water and 10–100,000 parts by weight of the emulsifier, per part by weight of difluprednate.

3. The emulsion of claim 1, comprising 10–10,000 parts by weight of oil, 100–50,000 parts by weight of water and 10–10,000 parts by weight of the emulsifier, per part by weight of difluprednate.

4. The emulsion of claim 1, comprising 10–5,000 parts by weight of oil, 500–50,000 parts by weight of water and 10–5,000 parts by weight of the emulsifier, per part by weight of difluprednate.

5. The emulsion of claim 1, wherein the fatty acid ester of glycerol is a member selected from the group consisting of castor oil, peanut oil, cotton seed oil, soybean oil, olive oil and a medium chain fatty acid triglyceride.

6. The emulsion of claim 1, wherein the emulsifier comprises a surfactant.

7. The emulsion of claim 6, wherein the surfactant is a nonionic surfactant.

8. The emulsion of claim 7, wherein the nonionic surfactant is a member selected from the group consisting of polyoxyethylene hydrogenated castor oil and a polyoxyethylenesorbitan fatty acid ester.

9. The emulsion of claim 8, wherein the polyoxyethylenesorbitan fatty acid ester is a member selected from the group consisting of polyoxyethylenesorbitan monooleate, polyoxyethylenesorbitan monolaurate, polyoxyethylenesorbitan monopalmitate and polyoxyethylenesorbitan monostearate.

10. The emulsion of claim 1 which is an oil-in-water type emulsion.

11. The emulsion of claim 1 which is in the form of an eye drop, a nasal drop or an ear drop.

12. The emulsion of claim 2, which is an oil-in-water type emulsion.

13. The emulsion of claim 3, which is an oil-in-water type emulsion.

14. The emulsion of claim 4, which is an oil-in-water type emulsion.

15. The emulsion of claim 2, which is in the form of an eye drop, a nasal drop or an ear drop.

16. The emulsion of claim 3, which is in the form of an eye drop, a nasal drop or an ear drop.

17. The emulsion of claim 4, which is in the form of an eye drop, a nasal drop or an ear drop.

* * * * *

EX PARTE REEXAMINATION CERTIFICATE (4940th)

United States Patent
Kimura et al.

(10) Number: US 6,114,319 C1
(45) Certificate Issued: May 18, 2004

(54) COMPOSITIONS CONTAINING DIFLUPREDNATE

(75) Inventors: Masako Kimura, Kakogawa (JP); Shin-ichi Yasueda, Kobe (JP); Masazumi Yamaguchi, Kobe (JP); Katsuhiro Inada, Kobe (JP)

(73) Assignees: Senju Pharmaceutical Co., Ltd., Osaka (JP); Mitsubishi Chemical Corporation, Tokyo (JP)

Reexamination Request:
No. 90/006,548, Feb. 13, 2003

Reexamination Certificate for:
Patent No.: 6,114,319
Issued: Sep. 5, 2000
Appl. No.: 09/076,124
Filed: May 12, 1998

(51) Int. Cl.$^7$ ............................................. A61K 31/56
(52) U.S. Cl. ...................... 514/177; 514/912
(58) Field of Search ................................. 514/177, 912

(56) References Cited

FOREIGN PATENT DOCUMENTS

JP   5-43465   2/1993

OTHER PUBLICATIONS

*The Merck Index*, 12$^{th}$ Ed., p. 1308, 7742 (1996).

*Primary Examiner*—Frederick Krass

(57) ABSTRACT

The present invention relates to a liquid composition comprising difluprednate, oil, water and an emulsifier. The composition of the present invention has superior antiinflammatory action and antiallergic action. The composition of the present invention shows superior transfer to a lesion and uniform drug distribution upon administration, as compared to conventional preparations containing difluprednate, so that it shows sufficient efficacy in a smaller dose. The inventive composition is associated with extremely less uncomfortable feeling and foreign sensation upon administration, as compared to conventional preparations containing difluprednate, and it can be administered easily to local sites of eye, nose, ear and the like.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, lines 8–21:

Sterile purified water was heated to about 70° C. and polysorbate 80 (*polyoxyethelyene (20) sorbitan monooleate*), concentrated glycerol, sodium acetate, boric acid, sodium edetate and sorbic acid of the above formulation were added and dissolved. Its pH was adjusted to 6.0 with sodium hydroxide to give an aqueous phase. Separately, castor oil was heated to about 70° C. and difluprednate was added and dissolved to give an oil phase. The oil phase was added while stirring the aqueous phase with a homomixer to give a crude emulsion. This crude emulsion was finely divided in a microfluidizer and sterilized by filtration to give a composition of the present invention. The median size of the oil drop in the composition of the present invention was 0.06 µm.

AS A RESULT OF REEXAMINATION, IT HAS BEEN DETERMINED THAT:

Claims 5, 11 and 15–17 are cancelled.

Claim 1 is determined to be patentable as amended.

Claims 2–4, 6–10 and 12–14 dependent on an amended claim, are determined to be patentable.

New claim 18 is added and determined to be patentable.

1. A difluprednate emulsion *in the form of an eye drop, a nasal drop or an ear drop* comprising (*a*) difluprednate, (*b*) *an* oil [comprising a fatty acid ester of glycerol] *selected from the group consisting of castor oil, peanut oil, cottonseed oil, soybean oil, olive oil and a medium chain fatty acid triglyceride,* (*c*) water and (*d*) an emulsifier.

*18. A difluprednate emulsion in the form of an eye drop, a nasal drop or an ear drop comprising difluprednate, castor oil, water and polyoxyethylene (20) sorbitan monooleate.*

\* \* \* \* \*